United States Patent
Heimberger et al.

[11] Patent Number: 5,772,578
[45] Date of Patent: Jun. 30, 1998

[54] ENDOSCOPIC INSTRUMENT

[75] Inventors: Rudolf Heimberger, Oberderdingen; Helmut Heckele, Knittlingen; Uwe Schaumann, Villingen-Schwenningen; Ralf Burkhardt, Sulzfeld, all of Germany

[73] Assignee: Richard Wolf GmbH, Knittlingen, Germany

[21] Appl. No.: 714,739

[22] Filed: Sep. 16, 1996

[30] Foreign Application Priority Data

Sep. 14, 1995 [DE] Germany .................. 195 34 112.0

[51] Int. Cl.$^6$ ...................................................... A61B 1/00
[52] U.S. Cl. .................... 600/139; 600/141; 600/142
[58] Field of Search ................................ 600/139, 141, 600/142, 143, 144, 146, 149, 150, 153

[56] References Cited

U.S. PATENT DOCUMENTS

| | | |
|---|---|---|
| 4,353,358 | 10/1982 | Emerson .................................. 600/139 |
| 4,580,551 | 4/1986 | Siegmund et al. ...................... 600/139 |
| 4,790,294 | 12/1988 | Alfred, III et al. . |
| 4,802,461 | 2/1989 | Choe ................................... 600/139 X |
| 4,911,148 | 3/1990 | Sosnowski et al. . |
| 5,168,864 | 12/1992 | Shockey . |
| 5,271,381 | 12/1993 | Ailinger et al. . |
| 5,284,128 | 2/1994 | Hart ............................................. 128/4 |
| 5,299,562 | 4/1994 | Heckele et al. ...................... 600/146 C |
| 5,325,845 | 7/1994 | Adair ................................... 600/149 X |
| 5,448,989 | 9/1995 | Heckele .................................. 600/142 |

FOREIGN PATENT DOCUMENTS

| | | |
|---|---|---|
| 0 521 595 A2 | 1/1993 | European Pat. Off. . |
| 1347596 | 11/1963 | France ................................... 600/139 |
| 44 14810 C1 | 8/1995 | Germany . |
| 2 130 885 | 6/1984 | United Kingdom . |

*Primary Examiner*—Beverly M. Flanagan
*Attorney, Agent, or Firm*—Panitch Schwarze Jacobs & Nadel, P.C.

[57] ABSTRACT

An endoscopic instrument is disclosed which comprises a shank with a bendable region. The bendability is achieved by almost complete circumferential transverse recesses which form segments bendable to each other. To increase the robustness of the shank, the segments, at their free ends, are provided with guides which engage a neighbouring recess and are adapted to the contour of the shank. Furthermore in the lateral regions of the shank there are incorporated positive locking elements, which prevent the overloading of the shank on over-extension.

14 Claims, 4 Drawing Sheets

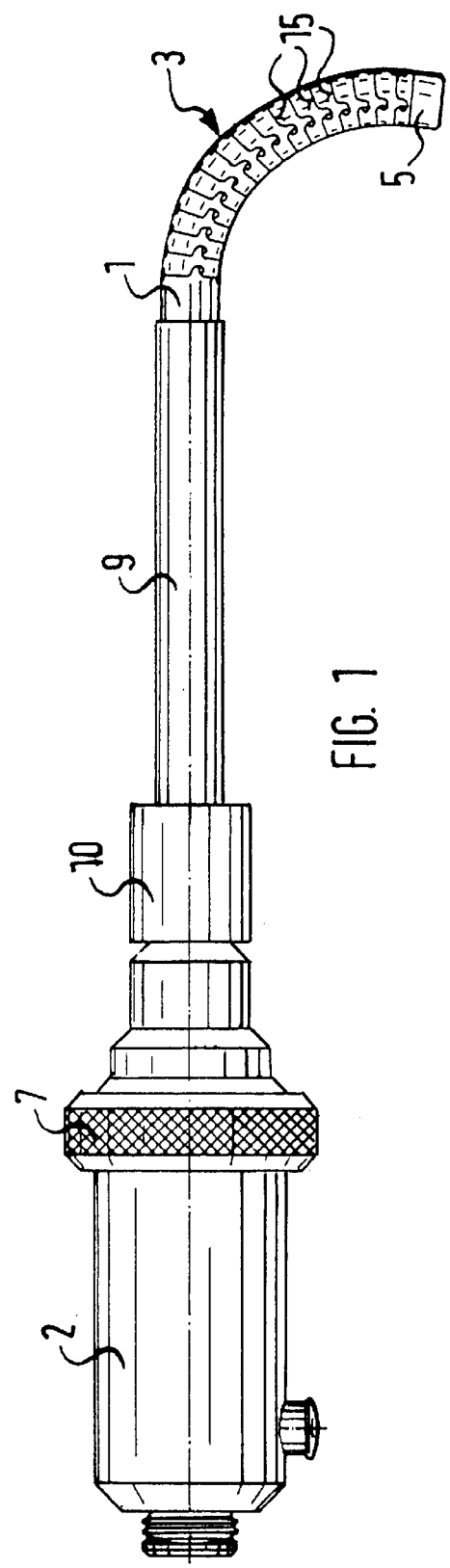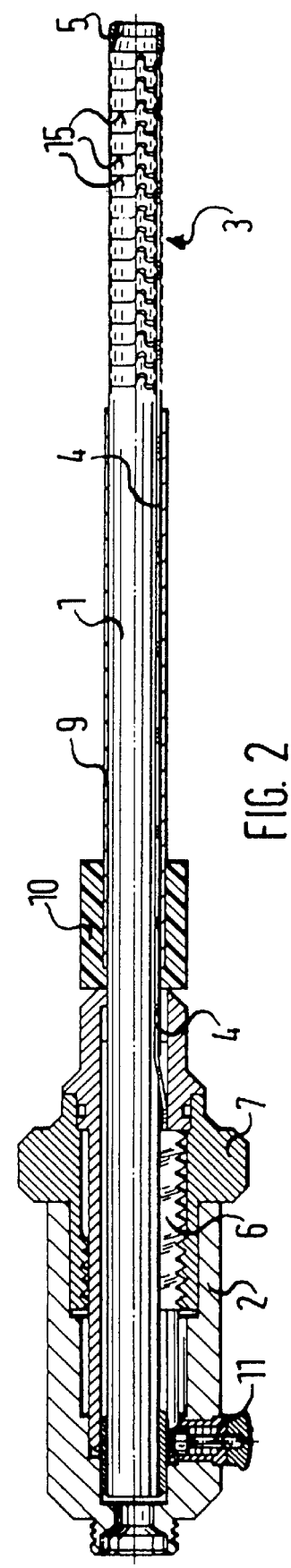

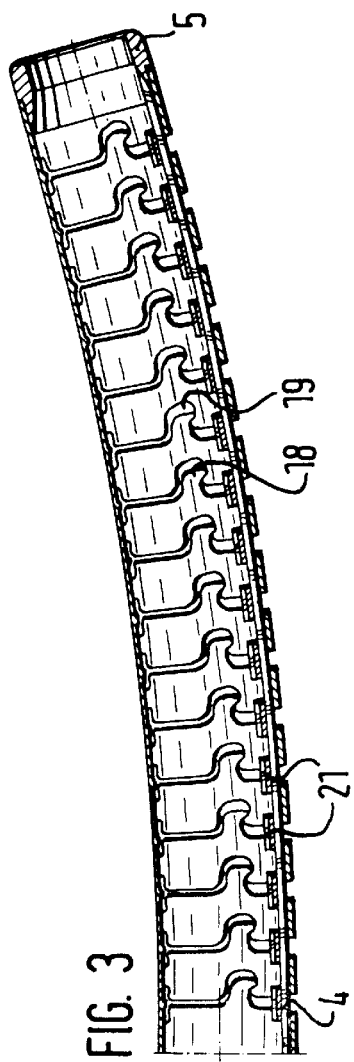
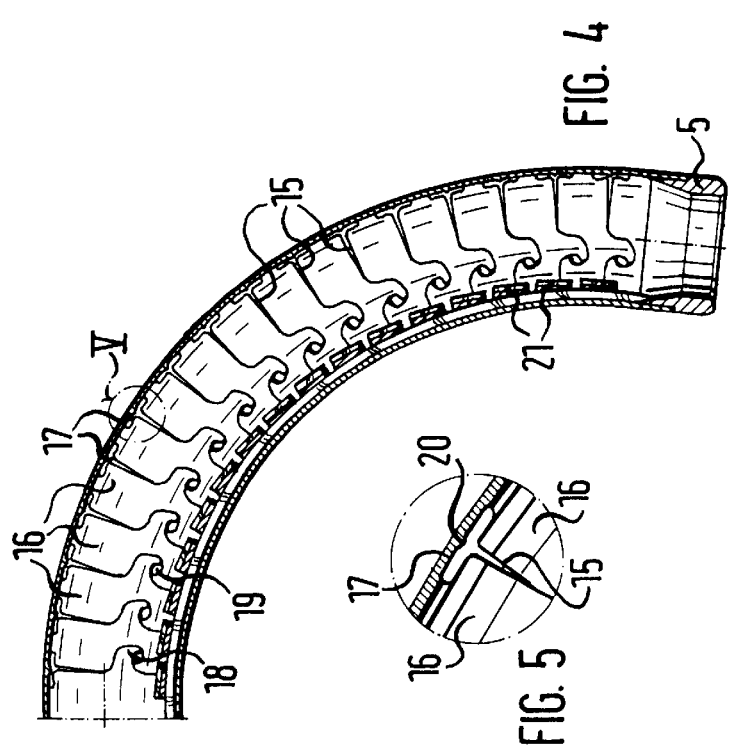
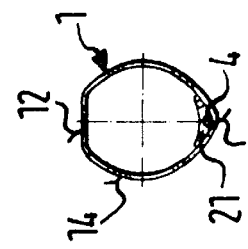

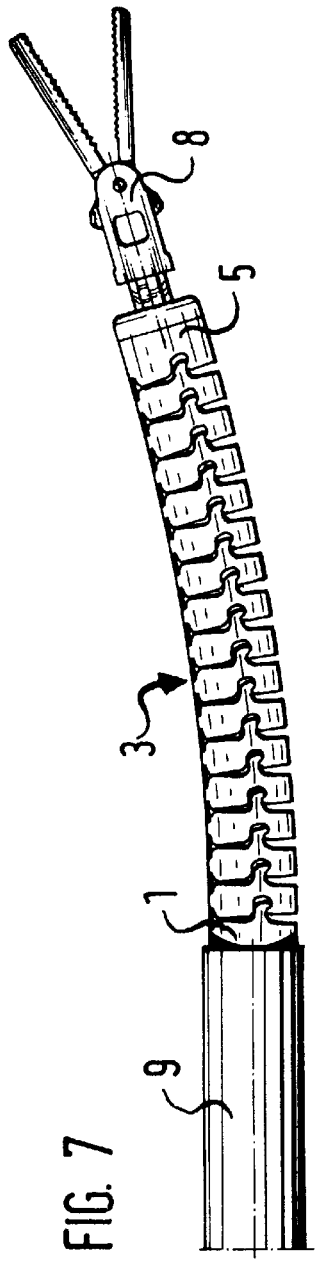
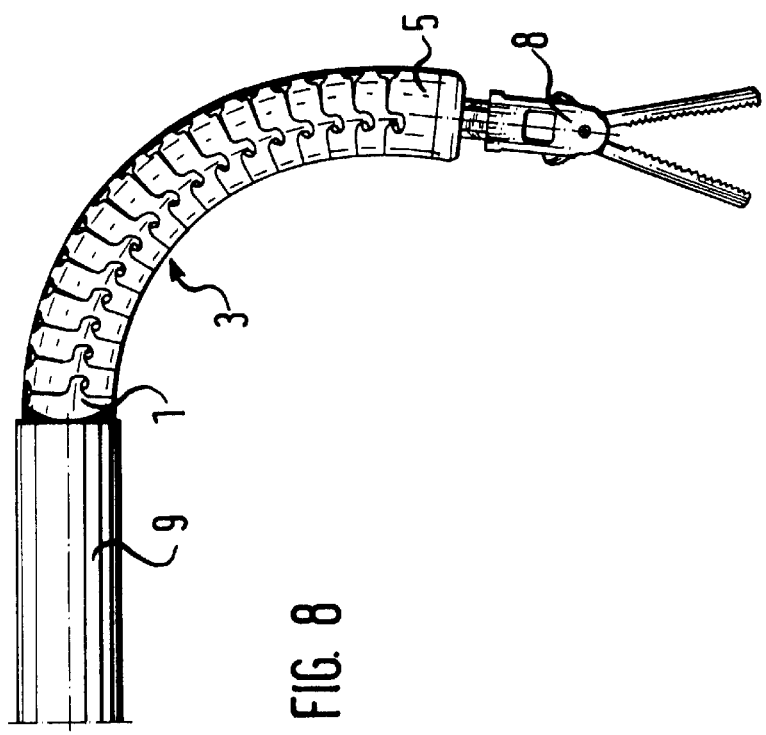
FIG. 7
FIG. 8

ENDOSCOPIC INSTRUMENT

BACKGROUND OF THE INVENTION

The invention relates to a bendable endoscopic instrument having a shank which, at its bendable region, is provided with transverse recesses dividing the bendable region into segments, the transverse recesses extending over a circumferential angle of more than 270°, and having a tension means running longitudinally across the recesses for controlling bending from the proximal end of the instrument

DESCRIPTION OF THE PRIOR ART

An instrument of the type according to the preamble is for example disclosed in GB-A-2130885. With the endoscopic instrument described here, the shank comprises at its distal bendable end region a multitude of transverse recesses which extend over nearly all of the shank circumference, and which divide this circumference into individual segments which are connected to one another by webs of the shank remaining at the ends of the recesses. Lying opposite these webs there is arranged a control wire running transversely over the recesses along the shank, the control wire being fastened on the one hand to the distal instrument end and on the other hand to a control provided in the handle part arranged at the proximal side. With this control the effective length of the tension wire may be changed, by which means the distal shaft region may more or less be bent. At the same time the transverse recesses achieve the necessary free space, in order to permit bending whilst having a comparatively rigid shank. This principle is known for endoscopic instruments, for example also from EP-A2-0521595 or U.S. Pat. No. 4,911,148.

Common to all these designs is that the shank, with an increasing bendability, i.e. with an increasing number of transverse recesses and with an increasing circumferential angle of the transverse recesses, becomes more unstable. There is the danger of a lateral buckling, this occuring outside the directed bending plane. Furthermore there is the danger that the shank is bent in another direction beyond its extended position, that is opposite to the directed bending direction. Then generally permanent deformations arise at the web regions of the shank, which after a short time may lead to a breakage of the shank. Finally such shanks also have only a limited torsional strength.

A further considerable disadvantage which actually all flexible shanks have is to be seen in that although the degree of bending may be set by fixing the tension means, such a bent shank however remains inherently flexible, i.e. it can be pivoted within the fixed bending region, so that for example regions of larger and smaller bending result. In many cases however it would be desirable to have a flexible or bendable shank which, after the bending has been effected, behaves like a bent rigid tube.

SUMMARY OF THE INVENTION

Against the background of this prior art it is the object of the invention to design a bendable endoscopic instrument of the type according to the preamble, using simple design means, such that the previously mentioned disadvantages are more or less avoided and an inherently stiff an instrument as possible is formed. In a further embodiment, this instrument may be fixed in its respective bending such that it behaves like a rigid bent tube.

This object is achieved by the shank, at least at its bendable region, having a cross-section which is flattened at one side with the shank assuming a link function at the flattened region, and by the tension means being arranged in guides on the side lying opposite the flattened region, the guides being adapted to the inner contour of the shank in this region, spanning a transverse recess in each case and being firmly attached to a segment at one side of the spanned recess. The object is further achieved by arranging in the shank between neighboring segments positive locking elements which limit the pivoting angle.

According to the invention guides are provided which are adapted to the shank cross-section in this region and are so designed in a longitudinal manner that in each case they span a recess. At the same time said guides are firmly attached to only one segment so that as a result, a telescopic type guide is achieved which considerably increases the torsional strength of the shank.

Furthermore, the invention provides for incorporating positive locking elements in the shank between the tension means guide and the flattened region between neighbouring segments, these elements limiting the pivoting angle, particularly in the overextended direction. These positive locking elements are to be arranged as close to the guide as possible, and are thus arranged at a distance from the flattened region, in order to achieve a large as possible safety against buckling over the predetermined allowable bending. The positive locking elements are preferably formed by the transverse recesses; this saves space and is economic at the same time, should the transverse recesses for example be manufactured by laser cutting or spark erosion.

According to the invention the shank is provided not with the usual round profile, but with an essentially oval cross-sectional profile flattened on one side. With this, the flattened profile parts form the link locations in the region of the transverse recesses. With this choice of profile of the shank there results not only advantages of stability but also advantages in the spacial arrangement. Since the instruments which are to be guided through the shank are generally of a circular cross section, the region towards the point lying opposite the flattened point may be used for the space saving arrangement of the tension means. These tension means which in any case are to be guided within the shank, are, according to the invention, mounted in guides in this region, these guides not only guiding the tension means to one another but also guiding the segments formed by transverse recesses.

The positive locking elements are preferably formed by hook shaped formations in the lateral wall of a segment as well as by corresponding formed reliefs, contoured with a clearance, in the lateral wall of the neighbouring segment. Such a hook shaped projection may also be provided at two sides of each positive locking element in order to accommodate a larger force.

In order to achieve a small as possible loading of the force introduction in the web, said web assumes a link function and being formed by the flattened part between two segments, the recesses have a T-shaped run out section to both sides of the flattened shank region so that there arises not a point buckling location, but a bending region and it is ensured that the bending of this region, in the case of the bending of the instrument, remains in the elastic region. Preferably the recess is formed running back at the crossing point of the T in order to avoid a load accumulation at this point.

The guides which guarantee a high torsional strength of the shank also in the bendable region, are preferably formed from sheet metal as punched and/or flexional form parts and are connected to the accompanying segment by point welding. Within the meaning of this invention, point welding is understood not to mean resistance point welding but an essentially point shaped material fit connection, such as is effected by an electron beam or laser welding. Moreover the connection may of course be effected over the whole surface or only at the edge region, but with modern manufacturing processes however the point shaped connection is particularly economic, and adequately meets the requirements of strength. Likewise the guides may be economically cut from profiled material.

The guides preferably serve not only the guiding of the segments in their free region, but also, at the same time, the guiding of the tension wire. As such it is not absolutely necessary that the tension means is directly guided in the guides, but they may be guided through the free space remaining between the guides and the shank. Otherwise not only tension means but also for example fibre optics may be guided through these guides.

The previously mentioned measures, in particular with regard to the oval and one sided flattened profiling of the shank, to the guides on the side of the shank opposite the flattened side as well as to the positive locking elements laterally arranged between these regions, each increase the stability of the shank. Preferably these measures are effected combined in order to not only increase the individual characteristics, such as torsional and bending strength, but also the total stability of the shank.

The control of the bending is effected via the tension means which is attached on the one hand to the distal end of the shank and on the other hand to a control part on the proximal side which is displaceably mounted in a handle part attached to the shank. This control part preferably comprises external toothing which combs with the internal thread of a knurled nut rotatably mounted in the handle part. The bending or extension of the instrument may be effected continuously by simple rotation of the nut in the handle part, whereby it is designed such that there is self-locking, i.e. a set angle may not be changed by influences from the distal end of the instrument.

Although, in the previously designed manner the angle as such may be fixed, the angular position of the individual segments to one another remain changeable, so that the bendable shank region has a certain flexibility which is not always desirable. In order to bring this bent shank region into a rigid form after having effected the setting of the bending, the invention provides for a tensioning tube which tensions those segments which are pivotable to one another. The tensioning is effected in that a tube which surrounds the shank and spans the region between the handle part and the bendable region is pushed so far in the distal direction that a tensioning is effected with regard to the tension means. This tensioning tube can be fixed in its tensioned position and when required released again.

BRIEF DESCRIPTION OF THE DRAWINGS

The invention is hereinafter described in more detail by way of the embodiment examples disclosed in the drawings. These show:

FIG. 1 a lateral view of an endoscopic instrument with a bent shank end,

FIG. 2 a longitudinal section of the instrument according to FIG. 1, with an extended shank end, FIG. 3 an enlarged representation of the bendable distal end of the shank of the instrument according to FIGS. 1 and 2 in a first angular position, FIG. 4 a representation according to FIG. 3 of the shank end in a second angular position, FIG. 5 an enlarged representation of the detail V in FIG. 4, FIG. 6 the shank cross-section in the bendable region, FIG. 7 the bendable distal end of the shank with a forceps located therein, in a first position, FIG. 8 the instrument according to FIG. 7 in a second position and FIGS. 9 to 11 a lateral view of two neighbouring segments of a further shank embodiment, in three different positions.

DETAILED DESCRIPTION OF THE PREFERRED EMBODIMENTS

Figure 9:
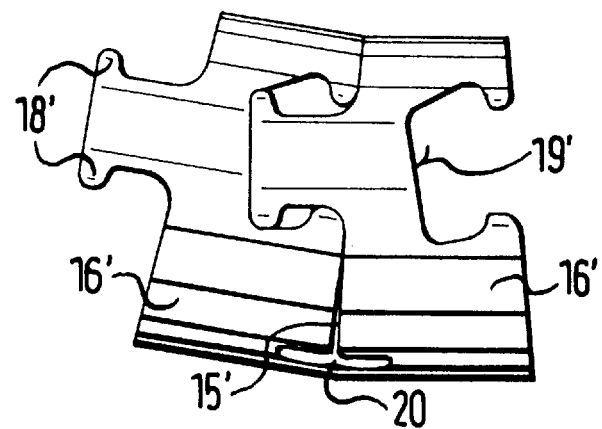

The endoscopic instrument represented comprises a shank 1 which is fixed within a handle part 2 at the proximal side. The shank 1 is rigidly formed upto its distal end region 3. The distal end region 3 on the other hand is bendable. For controlling the distal end region 3 which is bendable in one plane (with those embodiments shown, in the plane of the drawings) a tension-push wire 4 is guided within the shank 1, said wire being fastened to the distal end 5 of the shank 1 on the one hand, and on the other hand to a slider 6 which is arranged within the handle part 1 and is displaceable out of the shank 1. The slider 6 guided within the handle part 2 comprises toothing on its side facing the outside, said toothing combining with the internal thread of a knurled nut 7 rotatably mounted on the handle part 2. By turning the knurled nut 7, the slider 6 is longitudinally displaced on the shank 1 by which means the effective length of the wire 4 is altered and the bending in the distal end region 3 is set. The shorter the effective length of the wire 4, the larger the bending. Since the wire 4 may not only transmit tensional forces but also push forces, the shank 1 may not only be brought into its extended position (FIG. 2) but also into an over-extended position (FIG. 3).

A flexible endoscope or a flexible endoscopic instrument, for instance a forceps 8, may be guided through the hollow shank 1, as is shown for example by way of FIGS. 7 and 8. On guiding through an endoscopic instrument it is important that the shank 1, after effecting the bending, is as rigid as possible also in its bendable end region 3, so that the flexible forceps 8 or another instrument may be able to be guided precisely, if for example such a bending is required for going around a blood vessel or an organ. In order to ensure this, a sleeve 9 which is axially displaceable on the shank 1 is arranged as a tensioning tube on said shank. On the proximal side, this sleeve 9 comprises a handle part 10 with which said sleeve is axially displaceable on the shank 1. In order to fix the shank 1, and in particular the bendable end region 3, in the angular position as for example shown in FIGS. 1, 3 and 4, the sleeve 9 is pushed distally as far as possible using the handle part 10, by which means the proximal part of the end region 3 is tensioned against the force of the wire 4 within the tensioning tube 9. Using this measure, the end region 3 becomes practically rigid in the respective angular position.

In particular, with a corresponding shape profiling of the shank 1 and the tensioning tube 9, which is represented for the shank 1 by way of FIG. 6 and is described in detail hereinafter, the tensioning tube stops automatically at the position which fixes the shank 1. However, where appropriate, to support this, a latcher may be provided in the handle part 10. Between the actual handle part 2 and the handle part 10 a helical compression spring or other spring means may also be provided, should the end region 3 automatically be brought into a rigid position. Then, for the purpose of adjusting the bending, by way of the knurled nut 7, the tensioning tube 9 is first to be pulled back against spring force.

For cleaning purposes the previously mentioned components may be detached from one another by way of removing the blocking pin 11 represented by way of FIG. 2. The handle part 2 can then be dismantled into its front and rear parts, the knurled nut 7 removed from the front handle part 2 and the shank 1 which is coherent with the wire 4 and slider 6, removed. The tensioning tube 9 can be pulled off over the distal end 5.

The shank 1 has an essentially oval cross-section, as can be seen from FIG. 6. At one tip of the oval the shank 1 is flattened—the flattened region is indicated at 12, and lying opposite to this, said shank is formed pointed—this region is indicated at 13. Comparatively flat arched regions 14 extend between the flattened region 12 and the pointed region 13.

In order to be able to bend the shank 1 in the end region 3, a multitude of circumferential transverse recesses 15 are arranged behind one another in the longitudinal direction of the shank and which in this embodiment extend of a circumferential angle of about 300°, this being over the whole circumference of the shank with the exception of the flattened region 12. In this way, tubular segments 16 are formed which in the region of the transverse recesses 15 are only connected by a remaining flat web 17. The transverse recesses 15 run essentially in a straight line transverse to the longitudinal axis of the shank 1, but in the lateral regions 14, and specifically near to the pointed region 13, are approximately designed in the shape of a hook, so that in each case two hook shaped 18 projections and two correspondingly contoured recesses 19 are formed at neighbouring segments 16.

Each hook shaped projection forms, with the accompanying recess 19 into which it engages, a positive locking element. These positive locking elements ensure that the shank may not be bent beyond the predetermined maximum bending or may not be over-extended. This is important, in order to protect the webs 17 which in each case form a link for the segment 16, against permanent deformation and thus prevent a premature breakage. In particular, in the direction of an over-extension (see FIG. 3 and FIG. 7) these webs 17 are vulnerable. Here, the inner side of the hook shaped projections 18, in combination with the side of the recesses 19 which face this said side, form a stop. The further this pair of surfaces are displaced towards the pointed region 13, the greater become the forces which may be accommodated thereby. In the opposite direction, i.e. in the predetermined direction of bending (see FIG. 4 and 8) there results a stop function using the edges of the recesses 9 in the pointed region 13. This may however be supported further in this direction by the hook shaped projections 18 in combination with the corresponding recesses 19.

In order to prevent an excessive elongation of the web region 17, a transverse recess 15 does not directly run towards the flattened region 12, but here is T-shaped in such a manner that the web 17 is enlarged in the axial direction of the shank 1. In this way the bending angle may be increased since the bending is spread over a larger region. Furthermore the recess 15 is so formed in this T-shaped run out region that roughly at the crossing point of the T, a shaft region remains projecting in the direction towards the recess 15, the recess thus runs back in this region. In this way, the directed accumulation of material in the middle of the web 17 is effected, by which means this otherwise critical region is reinforced.

In order to further stabilize the shank 1 in the bendable region, in particularly to increase the torsional strength, each segment 16 in the pointed cross-section region 13 comprises a guide 21 which is fixedly attached to the segment, said guide spanning a neighbouring transverse recess 15. The guides 21 are formed from sheet metal with the embodiment form shown, this metal being adapted to the inner contour in the pointed region 13 so that it only permits a predetermined bending movement in the plane of the drawing. As the cross-sectional representation according to FIG. 6 shows, the guide 21 comprises approximately the cross section of a flat triangle, whereby in the pointed region 13 there is provided a recess through which the wire 4 is guided. Neighbouring this on the left and the right, there are provided two smaller recesses, in which in each case a fibre optic is guided. The fibre optics may for instance be unordered fibre bundles for transmitting illumination light or ordered fibre bundles for picture transmission or also each a fibre optic bundle for transmitting illumination light and a picture conductor bundle for picture transmission. The remaining free space within the shank 1 has roughly a circular form, disregarding the flattening 12. The guides 21 thus not only embody a guide for the segments 16, but also at the same time a guide for the wire 4 which is either guided within the guides 21 or between the guides 21 and the shank 1.

Figure 10:
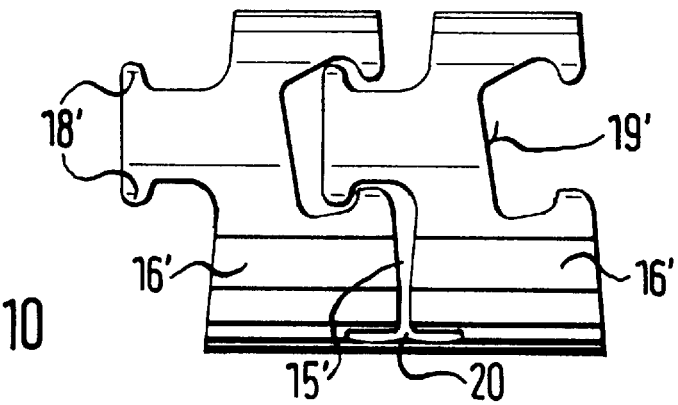
Figure 11:
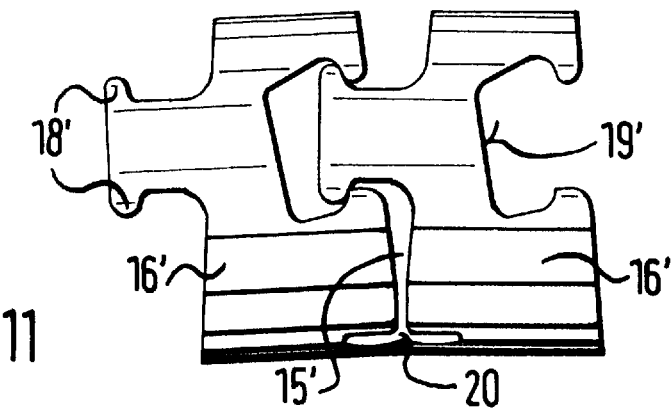

An alternative design of two segments 16' is shown by way of FIGS. 9 to 11, and specifically, in FIG. 9 in a position of maximum bending (corresponding roughly to a bending as is shown in FIGS. 4 and 8), in FIG. 10 in an extended position and in FIG. 11 in an over-extended position (corresponding roughly to the over-extension as is shown by way of FIGS. 3 and 7).

The segments 16' are formed by transverse recesses 15' which differ from those previously described transverse recesses 15 in that in the lateral region, they form hook shaped projections 18' towards the flattened region 12 as well as towards the pointed region 13. The recesses 19' are correspondingly contoured. This shaping of projections 18' and recesses 19', which can be seen in detail in the figures, offers a particularly high safety against overloading in both directions (buckling and over-extending). The shaping is such that on maximum allowable bending (FIG. 9), neighbouring segments 16' lie adjacent one another over almost all of the lateral region 14, with the end faces facing one another.

In the other end position (FIG. 11), in which there is the danger of an over-extension, two hook shaped projections 18' lie adjacent corresponding projecting parts of each recess 19' by which means a uniform force transmission from two sides of the recess is effected. In all intermediate positions on the other hand, the segments 16' are freely movable to one another at these lateral regions. For a better overall view, the guides 21 are not shown in FIGS. 9 to 11.

Otherwise it can be clearly seen by way of FIGS. 9 to 11 as to how advantageous the projecting shank region 20 is with regard to the web loading.

What is claimed is:

1. A bendable endoscopic instrument comprising:
   a shank (1) having a bendable region (3) with transverse recesses (15) dividing said bendable region into segments (16), said transverse recesses extending over a circumferential angle of more than 270° and less than 360°, and comprising a tension means (4) longitudinally running across the recesses (15) for controlling bending from a proximal end;

the shank (1), at least at said bendable region (3), comprising a cross-section which is flattened at one side, and the shank (1) providing a link function at the flattened region (12);

tension means (4) being arranged in guides (21) on a side region (13) of the shank lying opposite the flattened region (12), said guides being adapted to the inner contour of the shank (1) in the side region (13), each guide spanning a neighboring transverse recess (15) and being firmly attached to a segment (16) at one side of the spanned recess (15).

2. An instrument according to claim 1, wherein positive locking elements (18, 19) limiting the pivoting angle arranged in the shank (1) between adjacent segments (16).

3. An instrument according to claim 2, wherein the positive locking elements (18, 19) are formed by transverse recesses (15).

4. An instrument according to claim 2, wherein the positive locking elements (18, 19) are arranged at both sides between the tension means guide and the flattened region (12) of the shank (1).

5. An instrument according to claim 1, wherein the shank (1) comprises an essentially oval cross-section flattened on one side.

6. An instrument according to claim 1, wherein a positive locking element is formed by a hook shaped formation (18) in the lateral wall (14) of a segment (16) as well as by a recess (19) correspondingly contoured with a clearance, said recess being in the lateral wall of the adjacent segment (16).

7. An instrument according to claim 1, characterized in that the transverse recesses (15) terminate towards the flattened shaft region (12) with a T-shaped section and preferably are formed running back at the crossing point of the T.

8. An instrument according to claim 1, characterized in that the guides (21) are formed from sheet metal and are connected to the respective segment (16) by point welding.

9. An instrument according to claim 1, characterized in that the tension means (4) is fastened at the distal side to the shank (1) and at the proximal side to a control part (6), said control part being displaceably guided in a handle part (2) connected to the shank (1).

10. An instrument according to claim 1, characterized in that the tension means (4) is also designed to transmit compression forces.

11. An instrument according to claim 1, wherein the shank (1) is provided with a tensioning tube (9) reaching from the handle part (2) up to near the bendable region (3), said tensioning tube being longitudinally displaceable to the shank (1) and fixable in its position to the shank (1).

12. An instrument according to claim 1, wherein the guides (21) guide and accommodate at least one optic fibre next to the tension means (4).

13. A bendable endoscopic instrument comprising a shank (1) having a bendable region (3) with transverse recesses (15) dividing said bendable region into segments (16), said transverse recesses extending over a circumferential angle of more than 270° and less than 360°, and comprising a tension means (4) longitudinally running across the recesses (15) for controlling the bending from a proximal end; and positive locking elements (18, 19) limiting a pivoting angle of adjacent segments arranged in the shank (1) between adjacent segments (16).

14. A bendable endoscopic instrument comprising a shank (1) having a proximal end and a distal end, the shank (1) having a bendable region (3) at the distal end thereof and a handle part (2) at the proximal end, a tensioning tube (9) extending from the handle part (2) to a position near the bendable region (3), said tensioning tube being longitudinally displaceable to the shank (1) and fixable in its position to the shank (1).

* * * * *